(12) United States Patent
Bowers, II et al.

(10) Patent No.: US 10,578,525 B2
(45) Date of Patent: Mar. 3, 2020

(54) CHEMICAL PRECONCENTRATOR WITH INTEGRATED HEAT SOURCE FOR ENHANCED CHEMICAL ANALYSIS

(71) Applicant: BAE SYSTEMS Information and Electronic Systems Integration Inc., Nashua, NH (US)

(72) Inventors: Michael J. Bowers, II, Sykesville, MD (US); John E. King, Ellicott City, MD (US); Tadd C. Kippeny, Pasadena, MD (US)

(73) Assignee: BAE Systems Information and Electronic Systems Integration Inc., Nashua, NH (US)

(*) Notice: Subject to any disclaimer, the term of this patent is extended or adjusted under 35 U.S.C. 154(b) by 131 days.

(21) Appl. No.: 15/667,667

(22) Filed: Aug. 3, 2017

(65) Prior Publication Data

US 2019/0041305 A1 Feb. 7, 2019

(51) Int. Cl.
*G01N 1/40* (2006.01)
*G01N 1/02* (2006.01)
*G01N 1/22* (2006.01)
*G01N 30/00* (2006.01)

(52) U.S. Cl.
CPC ............ *G01N 1/405* (2013.01); *G01N 1/02* (2013.01); *G01N 1/2214* (2013.01); *G01N 2001/022* (2013.01); *G01N 2001/028* (2013.01); *G01N 2030/008* (2013.01)

(58) Field of Classification Search
CPC ........ G01N 1/405; G01N 1/44; G01N 1/2214; G01N 2030/008; G01N 2030/027; G01N 2030/085; G01N 2030/484; G01N 30/08; G01N 30/482
See application file for complete search history.

(56) References Cited

U.S. PATENT DOCUMENTS

| 7,299,711 | B1* | 11/2007 | Linker ................. G01N 1/2214 73/863.23 |
| 7,931,788 | B1* | 4/2011 | Wilkins ............ G01N 33/5438 204/403.01 |
| 8,365,575 | B2 | 2/2013 | Kippeny |
| 8,833,140 | B2 | 9/2014 | Bowers, II et al. |
| 9,103,804 | B2 | 8/2015 | Badorrek et al. |
| 9,278,335 | B2 | 3/2016 | Sengupta et al. |
| 2003/0085348 | A1* | 5/2003 | Megerle ............... G01N 1/2202 250/287 |
| 2004/0131503 | A1* | 7/2004 | McGann ............ B01D 39/2051 422/78 |

(Continued)

OTHER PUBLICATIONS

Pelissier, K. et al. "Silicon carbide heating elements." Ceramics International (1998) 24 371-377. (Year: 1998).*

(Continued)

*Primary Examiner* — Christopher Adam Hixson
(74) *Attorney, Agent, or Firm* — Davis & Bujold, PLLC (57) ABSTRACT

A method for detection and identification of a chemical using a preconcentrator to collect a sample of the chemical, process said sample of the chemical, and introduce said processed chemical into a chemical analysis instrument for the detection of and identification of the chemical. A system for detecting and identifying a chemical comprising a preconcentrator having at least dual concentrating elements.

8 Claims, 6 Drawing Sheets

(56) References Cited

U.S. PATENT DOCUMENTS

| | | | |
|---|---|---|---|
| 2004/0157342 A1* | 8/2004 | Lovell | G01N 1/2202 |
| | | | 436/173 |
| 2011/0188702 A1* | 8/2011 | Haas | G06K 9/00 |
| | | | 382/100 |
| 2012/0073360 A1 | 3/2012 | Hunka et al. | |
| 2014/0017158 A1* | 1/2014 | Sengupta | C01B 32/05 |
| | | | 423/445 R |
| 2019/0060865 A1 | 2/2019 | Sengupta et al. | |
| 2019/0060866 A1 | 2/2019 | Bowers, II et al. | |

OTHER PUBLICATIONS

International Search Report, PCT/US2018/049486, dated Nov. 6, 2018, 9 pages.

* cited by examiner

CHEMICAL PRECONCENTRATOR WITH INTEGRATED HEAT SOURCE FOR ENHANCED CHEMICAL ANALYSIS

FIELD OF THE DISCLOSURE

The present invention relates to chemical analysis, and more particularly, to methods and apparatus for use in the preconcentration of samples for analytical chemistry.

BACKGROUND OF THE DISCLOSURE

Chemical detection and identification is typically a multi-step process, involving (1) collection of a sample, (2) processing of the sample, often including separation of chemicals in a chemical mix, (3) introduction of the processed chemicals into a chemical analysis instrument, and (4) detection and identification of any chemicals present in a sample. Each step requires different instrumentation, with an associated loss of at least some of the original sample. The multiple steps lead to reduced sensitivity in the overall process. A more efficient and cost-effective method for chemical detection and identification is, therefore, needed.

SUMMARY OF THE DISCLOSURE

According to an embodiment of the invention, the chemical preconcentrator comprises a single material that addresses the first three steps of the process and has the capacity to collect chemicals in all phases (gaseous, liquid, particulate, and aerosol) by adsorption. The preconcentrator separates chemicals during thermal desorption of the various chemicals into a chemical analyzer using a process of resistive heating. By using a single material for adsorption, separation, and introduction to an analyzer, the loss of sample is minimized.

In addition, the process may lead to a reduction in the size and/or weight of equipment necessary for chemical detection. Further, by starting with a monolithic material and forming the adsorbent material on the surface, the complications associated with cleanly attaching a sorbent material to a substrate are ameliorated resulting in maximum sorbent loading with no binders or other impurities which bleed and cause difficulty with trace analysis techniques.

One aspect of the present disclosure is a method for detection and identification of a chemical comprising the steps of: providing a preconcentrator configured for collecting a sample of the chemical; processing said sample of the chemical; introducing said processed chemical into a chemical analysis instrument; and detecting and identifying the chemical using said chemical analysis instrument.

One embodiment is wherein the preconcentrator comprises a solid substrate that can be resistively heated and which has a surface that can absorb and desorb chemicals. In some cases, the substrate and the surface comprise the same material. In certain embodiments, the substrate and the surface comprise silicon carbide foam. In some cases, the substrate and the surface comprise different materials. In certain embodiments, the substrate comprises carbide foam. In some cases, the surface comprises a carbide-derived carbon skin on said solid carbide foam.

Another embodiment is wherein the sample includes a single chemical. In some cases, the sample includes a plurality of chemicals. In certain embodiments, the sample is in a gaseous, liquid, particulate, or aerosol phase. In certain embodiments, the substrate is a solid surface, a fiber, a powder, open cell foam, or a mesh. In some cases, the substrate is patterned. In certain cases, both particulate and vapor samples are collected and analyzed simultaneously.

Another aspect of the present disclosure is a system for use in detecting a chemical comprising a power source; an inlet and an outlet; one or more proximity sensors configured to detect a proper testing distance; a motor control system for controlling an impeller attached to a motor; a dual concentrator element; an IR flash ring; and an air puffing unit.

In one embodiment, the system further comprises a rapid first alarm (RFA) detector and/or a docking station.

In certain embodiments, the dual concentrating element comprises a solid substrate that can be resistively heated and which has a surface that can absorb and desorb chemicals. In some cases, the substrate and the surface comprise silicon carbide foam. In some cases, the substrate and the surface comprise different materials. In certain embodiments, the surface comprises a carbide-derived carbon skin on said solid carbide foam.

These aspects of the disclosure are not meant to be exclusive and other features, aspects, and advantages of the present disclosure will be readily apparent to those of ordinary skill in the art when read in conjunction with the following description, appended claims, and accompanying drawings.

BRIEF DESCRIPTION OF THE DRAWINGS

The foregoing and other objects, features, and advantages of the disclosure will be apparent from the following description of particular embodiments of the disclosure, as illustrated in the accompanying drawings in which like reference characters refer to the same parts throughout the different views. The drawings are not necessarily to scale, emphasis instead being placed upon illustrating the principles of the disclosure.

DETAILED DESCRIPTION OF THE DISCLOSURE

In certain embodiments, the chemical preconcentrator consists of a solid substrate that can be resistively heated and a surface that can adsorb and desorb chemicals: In some cases, the substrate and surface may be the same material (e.g., solid silicon carbide foam) or may be different materials (e.g., a carbide-derived carbon (CDC) skin on solid silicon carbide foam). In certain embodiments, the substrate can be in any form that allows resistive heating. Some examples include solid (e.g., planar, porous) surfaces, open cell foams, meshes, and other patterned surfaces. The surface can adsorb and desorb a broad range of chemicals, one or more classes of chemicals, or specific chemicals. In some embodiments, the surface is stable under the conditions required for desorption (e.g., temperature and atmosphere) long enough to desorb chemicals.

In the adsorption phase, a chemical sample is introduced to the preconcentrator either by flowing the sample past or through the preconcentrator (in the case of gaseous, aerosol, or liquid samples) or by moving the preconcentrator into contact with the sample (e.g., for samples on surfaces such as liquids or particulates). The chemical sample may consist of a single chemical or a mix of chemicals.

In the chemical separation phase, the preconcentrator is heated by applying current to the substrate, which causes resistive heating. The heating causes the chemical sample to desorb from the surface of the preconcentrator. The sample is then transferred via a gas flow to another instrument for further processing or (more typically) for chemical analysis.

In some embodiments of the system of the present disclosure, the gas flow may consist of inert gas(es) (e.g., nitrogen or helium), reactive gas(es) (e.g., oxygen), or air. By varying the current applied to the substrate, the temperature of the preconcentrator can also be controlled. The temperature during the desorption cycle can be fixed or varied to enhance chemical separation. Usually the desorbed chemical sample is flowed directly into a chemical analysis instrument for characterization. Some examples of such instruments to which the preconcentrator can be directly interfaced include, but are not limited to, ion mobility spectrometers (IMS), differential mobility spectrometers (DMS), mass spectrometers (MS), and gas chromatography mass spectrometers (GC-MS).

This system of this disclosure combines chemical adsorption and separation in a single material. In some instances, the preconcentrator is incorporated into a single device that both adsorbs samples and separates the component chemicals during desorption into an analyzer. This eliminates the need for a separate instrument for chemical separation, resulting in a reduction in the size, weight, and cost of the overall system.

One embodiment of the system comprises a combined adsorber/desorber unit that utilizes a silicon carbide foam with a (carbide derived carbon) CDC surface as the preconcentrator. The adsorber/desorber unit was able to replace the GC unit on a commercial GC-MS because the CDC/silicon carbide preconcentrator had the capability to separate chemicals; moreover, the combined adsorber/desorber unit was smaller than the GC unit, even though it contained additional functionality (i.e., adsorption).

Even when separation of adsorption and desorption steps is necessary (e.g., adsorption in the field, desorption and analysis in the laboratory), the use of a single material to accomplish both tasks is advantageous because there are fewer chemical incompatibilities to deal with. It is understood that any material that adsorbs or interacts with a chemical has the potential to react with the chemical, cause the chemical to react with something else, or fail to release the chemical into the analysis instrument. In a standard GC-MS process, for example, an adsorbent material is used to adsorb the sample. The sample is then desorbed into a GC column, which separates the chemicals through a series of brief adsorptions and desorptions on the surface of the column; different chemicals are attracted to the column surface to a greater or lesser extent, causing some chemicals to pass through the column faster than others, resulting in chemical separation in time. However, the column may degrade certain chemicals or fail to deliver them to the analysis unit due to a chemical incompatibility, even if the chemicals were successfully desorbed from the initial adsorbent material (which has its own set of chemical incompatibilities). In contrast, by using a single material for both adsorption and chemical separation, the system of the present disclosure eliminates the need for a column and therefore a second set of chemical compatibilities. Thus, fewer of the chemicals in the original sample are lost to the adsorption/desorption/separation process.

Current adsorbents rely on external heating, which results in a temperature gradient within the adsorbent. The temperature gradient means that in some cases, not all chemicals are desorbed from the sample, and that the desorption profile in time is broad. This is why many chemical detection processes require an additional process for chemical separation. In contrast, by integrating resistive heating directly into the adsorbent material, the system of the present disclosure enables uniform heating of the entire material. More of the sample is therefore able to be desorbed, increasing the sensitivity of the total process, and the desorption profile of individual chemicals is more narrow in time, allowing for the elimination of a separate chemical separation step.

With the threat of ever increasingly inventive improvised explosive devices (IEDs), security checkpoints must have a means of rapid detection of a wide range of explosive materials at trace levels. To this end, the present system offers two solutions with the objective of new, non-contact sampling methods for enhanced sensitivity of ETDs (Explosive Trace Detectors) based on an air pulsed particulate extraction method combined with the rapid pre-concentration capability. In one embodiment of the system, a High Volume and Proximity Multi-Sampler (HVPMS) uses vacuum/pulsed air combined with an IR flash to retrieve particles from a variety of surface types and then simultaneously traps both trace particulates and vapors in our unique, porous foam within a dual concentrating element (DCE) for detection using conventional chemical analysis instruments.

One embodiment is a High Volume Multi-Sampler (HVMS) for air cargo type applications and another embodiment is a Proximity Sampler (PS) for next generation checkpoint type applications. Together, they form a High Volume and Proximity Multi-Sampler (HVPMS). The technology underpinning these samplers is a universal sorbent, carbide-derived carbon (CDC), that has been used to detect chemicals at concentrations down to 10 s of parts per trillion (ppt), thus enabling detection of even low-vapor pressure chemicals. To increase the probability of detection ($P_d$), the foam has been further engineered to adsorb particulates. Because the CDC adsorbs such a wide range of chemicals, it is not specific to one or a few explosives and does not need to be reengineered to address emerging threats. It can be used to detect not only current and future explosives and explosives precursors, but also narcotics as an added benefit.

The HVPMS addresses two mission relevant scenarios, non-contact screening at checkpoints and air cargo screening, by enabling non-contact (>2 inches from the surface), high-throughput (<5 s/sample) sampling on a variety of surfaces, surface areas, and operational scenarios to provide enhanced trace detection capabilities, with increased probability of detection ($P_d$) and decreased probability of false alarm ($P_{fa}$) while maintaining current ETD performance and life-cycle cost standards. The samplers are low cost and low power, with few consumables and >99.9% system availability. They are compatible with a wide variety of commercial detectors; thus, they can be used with the detectors currently in use at checkpoints, as well as any future upgrades that occur.

In certain embodiments, the HVPMS contains proximity sensors to enable consistent and accurate operation. The core technology used in the all-in-one adsorption and desorption dual concentrating element (DCE) rapidly concentrates and enables trace level detection (e.g., ppt) in a small size that enables high throughput sampling and desorption. In addition, the core technology is a broad sorbent that has been shown to adsorb (and subsequently desorb) a wide range of functional groups, thus enabling detection of a broad range of existing threats as well as future emerging threats.

Without the HVPMS system, operators cannot rapidly sample large surface areas and cannot effectively remove particles from textured surfaces or within cavities. Currently employed detection methods are highly dependent on operator training and cannot ensure consistent sampling. Furthermore, the sampling methods cannot be automated for cargo screening, do not address collection and transfer of both vapors and particles, and do not include concentration, all of which therefore limit the level of detection of trace explosives. Finally, contact sampling relies on consumables and cannot operate rapidly and continuously. In contrast, the HVPMS of the present disclosure enables operators to rapidly and reliably perform important check point and cargo screening with higher accuracy and fidelity then exists today, is compatible with a wide variety of detection methods, and is effective for detection of future threats.

Figure 1:
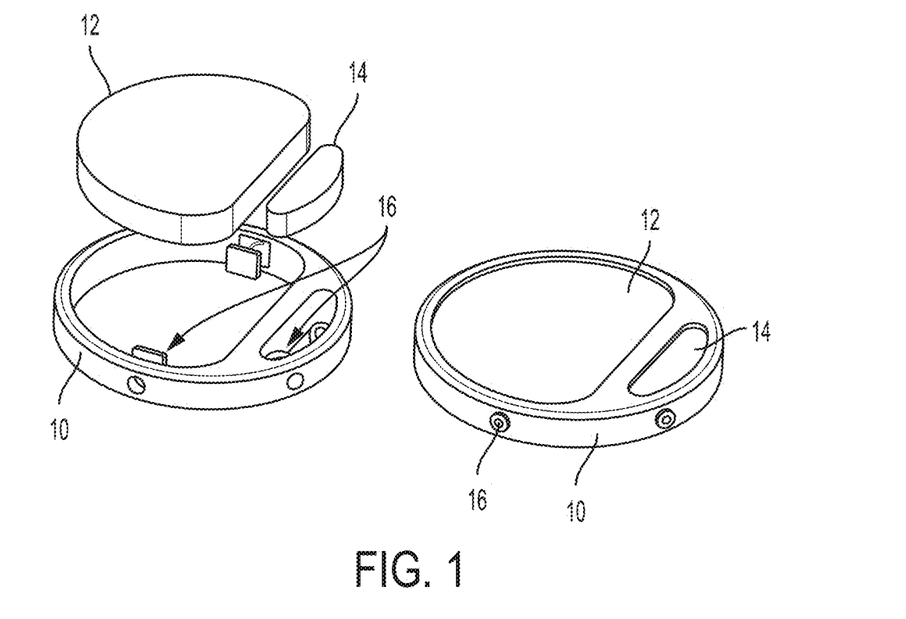
FIG. 1 shows a perspective view of one embodiment of a dual concentrating element (DCE) which employs SiC and CDC/SiC foams to capture both particles and vapors.

In certain embodiments, the HVPMS consists of two instruments, where the PS is a handheld unit that collects trace chemicals from people and small cargo, and the HVMS screens larger cargo and checked baggage. Both store the chemicals in reusable Dual Concentrating Elements (DCE) as shown in FIG. 1. The DCE interfaces with standard detection systems, such as mass spectrometers (MS) or ion mobility spectrometers (IMS), which detect and identify explosives and other chemicals. In some cases, an optional Rapid First Alarm (RFA) chemical detector provides the user with immediate detection of select explosives for rapid response.

Referring to FIG. 1, a perspective view of one embodiment of a dual concentrating element (DCE) which employs SiC and CDC/SiC foams to capture both particles and vapors is shown. More specifically, a base 10 is provided to support the adsorbent material(s). In one embodiment, a SiC foam 12 is used for particles and a CDC/SiC foam 14 is used for vapors. A series of electrical contacts 16 are also present on the base.

One key innovation of the PS and HVMS systems is the ability to collect and analyze both particulate and vapor samples simultaneously. This is made possible by leveraging a universal sorbent, CDC, to capture vapors in combination with a silicon carbide (SiC) element that collects particles much like a filter. The DCE holds the collected materials until introduction into the detector via thermal desorption activated by application of an electric current to the foam through electrical contacts 16. Both materials survive the high temperatures required to desorb particles, allowing the DCE to be recycled for 1000 s of uses. An added benefit of this heating arrangement is the ability to utilize staged desorption, allowing for separation of analytes pre-detector. The dual element format provides capture for vapor and particle samples in parallel so the air flow required for collection of the particles is not restricted.

Figure 2:
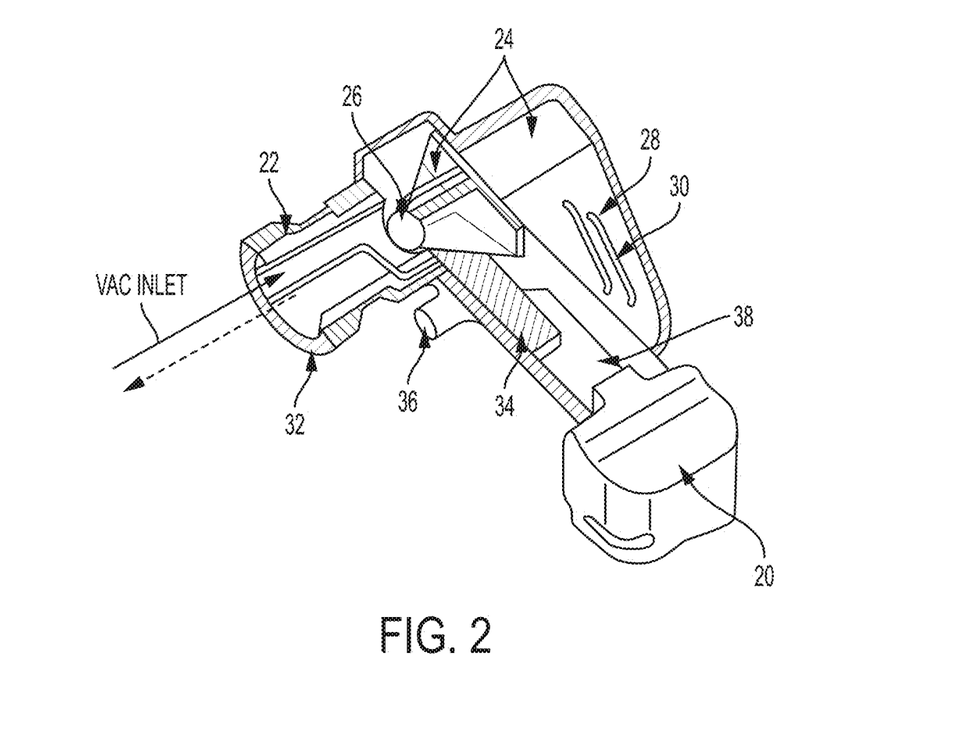
FIG. 2 shows a perspective view of one embodiment of a handheld proximity sampler (PS) which is designed for ease of use and high sensitivity.

Referring to FIG. 2, a perspective view of one embodiment of a handheld proximity sampler (PS) which is designed for ease of use and high sensitivity is shown. More particularly, the PS system is designed to sample all states of matter, including liquid and solid aerosols. The PS enhances non-contact surface sampling. Since stand-off particle sampling efficiencies from vacuum pressure alone will not suffice for trace explosives sampling, both air impingement and IR flash excitation are included in the PS to extract surface trace explosive compounds.

The PS has a rechargeable battery 20 and includes a proximity sensor 22 to help the user maintain adequate stand-off distance. In some cases, the proximity sensor is a capacitive proximity sensor. Dual proximity sensors give feedback to a motor control system 24 to keep the unit from inadvertently attaching itself to the surfaces being sampled. A rechargeable 18 V or 20 V Li-ion battery 20 provides several hours of operation. An efficient impeller spins on a Mil-Spec motor 24, creating between 60 and 100 CFM. Air is pulled through the DCE 26, past the impeller 24, through the exhaust plenum 28, and over a rapid first alarm (RFA) detector 30 before exiting the sampler. In certain embodiments, the PS weighs about 3.2-3.7 lbs. Assuming the IR flash is 100 W-s with one flash per 5 second sampling event, and assuming full use of the motor power, the PS will need 2 batteries per shift (100 samples per charge).

Still referring to FIG. 2, the PS comprises an IR flash ring 32 and a puffing unit 34. In some cases, the PS also has an ultrasonic proximity sensor 36. The PS may also contain a control CCA 38. A docking station (as seen in FIG. 3) is used for desorption (transfer) of samples collected by the PS into analysis instruments.

Figure 3:
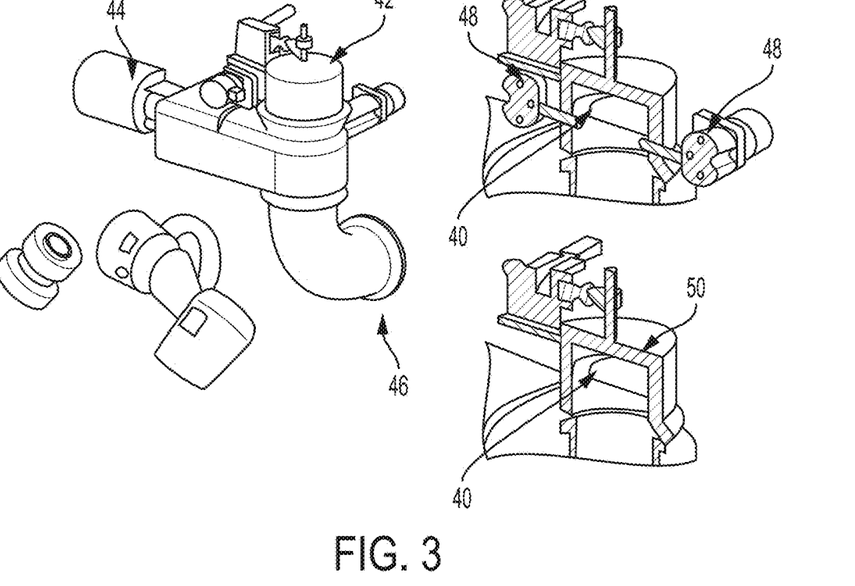
FIG. 3 shows a perspective view of one embodiment of a proximity sampler (PS) docking station variant for use with both MS (Mass Spec) and IMS (Ion Mobility Spec) detectors.

Referring to FIG. 3, a perspective view of one embodiment of a proximity sampler (PS) docking station variant for use with both MS (Mass Spec) and IMS (Ion Mobility Spec) detectors is shown. More specifically, the docking station comprises dual concentrator element 40; a lid 42; a valve 44; and an interface to the detector 46. In some cases, when the docking station is sued for a MS, vacuum valves 48 are present. In some cases, when the docking station is used with an IMS detector, an air vent 50 is present.

The station is system agnostic and can be adapted to any selected analysis system. FIG. 3 shows two variants of the docking station: a MS version that is designed to desorb under high vacuum, and a version designed for IMS that will desorb into an airstream. In some cases, the docking station attaches to the detector system, weighs 4.3 pounds, and consumes 54 W of detector-supplied power when in use. In some cases, a PS puck removal tool is also used.

Figure 4A:
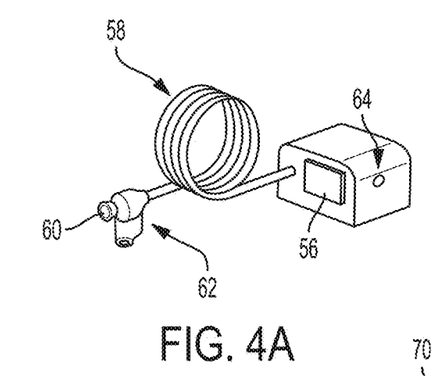
FIG. 4A-FIG. 4C shows a series of perspective views showing how one embodiment of the High Volume Multi-Sampler (HVMS) operates similarly to the proximity sampler (PS) but is designed for direct attachment to an analytical instrument, with more power for screening bulk cargo.
Figure 4B:
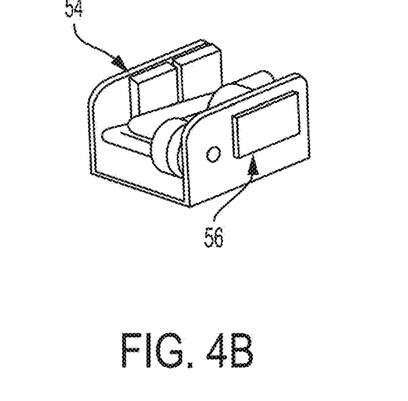
Figure 4C:
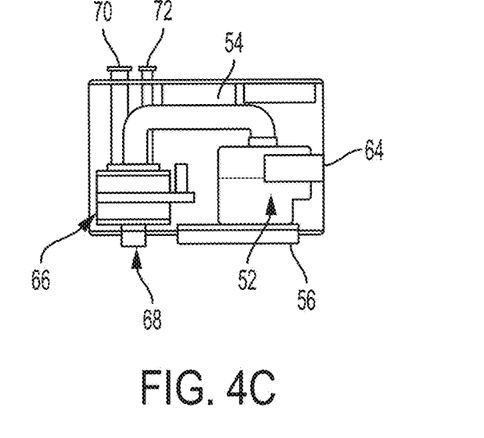

The operating principles of the HVMS (as shown in FIGS. 4A-4C) are similar to the PS. Referring to FIGS. 4A-4C, a series of perspective views showing how one embodiment of the High Volume Multi-Sampler (HVMS) operates similarly to the proximity sampler (PS) but is designed for direct attachment to an analytical instrument, with more power for screening bulk cargo is shown. More particularly, as best shown in FIG. 4C, the HVMS system incorporates a high-flow blower 52 with control and power supply electronics 54. As best shown in FIG. 4B, a touch screen system 56 acts as the user control interface.

In FIG. 4A, at the end of the sampling hose 58, a modified version of the PS 60 provides puffing and IR flash stimulus in order to enable sample collection. In this embodiment, a revolving cartridge assembly 66 consisting of multiple reusable DCEs is employed to provide high throughput (See, for example, FIGS. 5A and 5B). The PS is connected to the hose and has an impinging nozzle 62. The blower exhausts out of the unit 64 and the system has a high flow inlet 68. The analyte has an outflow port 70 and the Hi-Vac also has an outflow 72 on the unit.

Figure 5A:
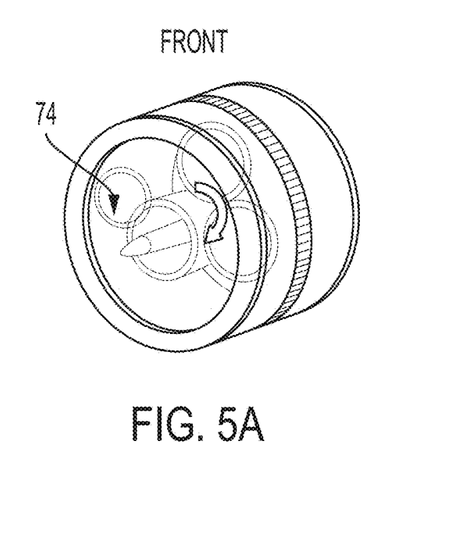
FIG. 5A shows a front perspective view of one embodiment of a revolving cartridge assembly which enables continuous scanning.
Figure 5B:
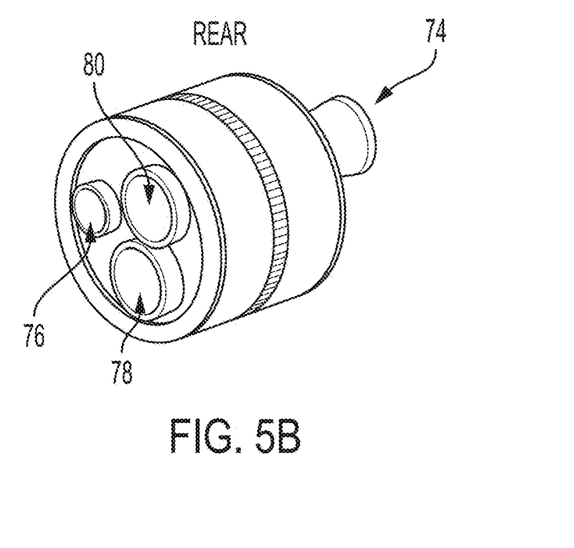
FIG. 5B shows a rear perspective view of one embodiment of a revolving cartridge assembly which enables continuous scanning.

Referring to FIG. 5A and FIG. 5B, one embodiment of the revolving cartridge assembly utilizes a rotating housing to move DCEs between three functional positions. FIG. 5A shows a front perspective view of one embodiment of a revolving cartridge assembly which enables continuous scanning. There, an inlet 74 is shown. FIG. 5B shows a rear perspective view of one embodiment of a revolving cartridge assembly which enables continuous scanning. The inlet 74 is shown as well as the connections for Hi-Vac 76, the analyzer 78, and the blower 80. In the sampling position, the DCE is exposed to the sampling input port, and a sample is drawn through the cartridge using a high-flow blower motor. In the desorption position, the DCE is rotated to align with the analyte output port, which connects to external analysis equipment.

Electric current is applied to the DCE for heating, and the collected materials are thermally desorbed in either vacuum or air flow stream, depending on the requirements of the analysis instrument. The final reconditioning stage exposes the DCE to high vacuum, and an applied current cleans the cartridge of residual material, preparing it for reuse. Using this assembly line methodology, <5 s sampling time can be achieved with minimal user intervention. The HVMS system, not including the sampling hose or head, measures approximately 14.5"×11.0"×9.0" and weighs <30 lbs. This ensures one-man lift compliance. When in use, the HVMS consumes a maximum of 720 W.

Figure 6A:
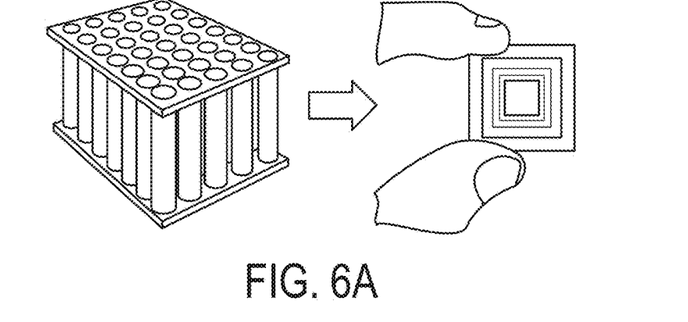
FIG. 6A shows a schematic diagram of SiN-VAPOR sensor (left) and prototype sensor assembly (right).

As an option, the PS or HVMS can be equipped with a selectable (ON/OFF) Rapid First Alarm (RFA) detector, which utilizes nanowires and nanotubes as field effect transistor-based chemical sensors (ChemFETs). This sensor is constructed with a Silicon Nanowire Vertical Array with PORous top electrode (SiN-VAPOR) architecture (See, for example, FIG. 6A).

Figure 6B:
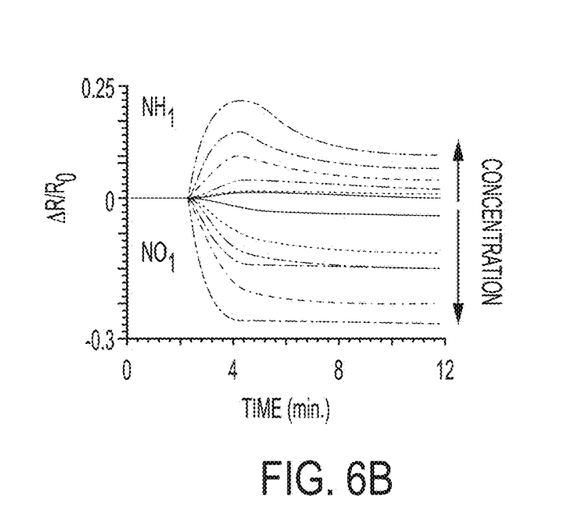
FIG. 6B shows a SiN-VAPOR response to $NH_3$ and $NO_2$ in moist air.
Figure 6C:
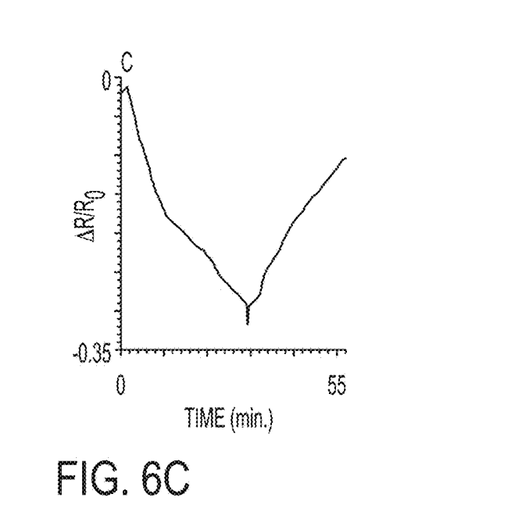
FIG. 6C shows the response to 340 parts per trillion TNT in moist air.

Referring to FIG. 6B, a response to trace $NH_3$ and $NO_2$ vapors confirms SiN-VAPOR's extreme sensitivity and speed. Referring to FIG. 6C, a response to trace TNT vapors confirms SiN-VAPOR's extreme sensitivity and speed. Analyte flow began at 2 minutes and stopped at 4 minutes and 31 minutes, respectively. A remaining critical attribute is selectivity in chemically complex environments. For this effort, selectivity is enhanced using a multipronged strategy including manipulation of the inherent nanowire properties, surface functionalization, and chemometrics to extract maximum information from the detector response.

Use of the PS and HVMS for non-contact sampling of trace explosives at security checkpoints provides improvement over current wipe technology by allowing rapid detection of a broad spectrum of threat agents without the need to make contact with passengers, luggage, or cargo, all while reducing operational costs by virtually eliminating consumables. This new operational paradigm requires a minimum of 50% throughput delivery of less than 50 ng of threat agent from a surface of interest to an analyzer of choice within 5 seconds.

The present system meets these requirements with the use of CDC as a universal adsorbent, which has proven itself in capturing and releasing trace threat agents for detection, and by intelligent airflow design to ensure rapid extraction and delivery of trace threat agents from a surface to an analyzer of choice. Demonstration of extraction and delivery of 1 ppm of vapor and 750 ng of doped particles with a 25% instrument throughput within 30 seconds is a starting point. Demonstration of extraction and delivery of 1 ppb of vapor and 50 ng of doped particles with a 50% instrument throughput within 5 seconds is also possible.

Figure 9:
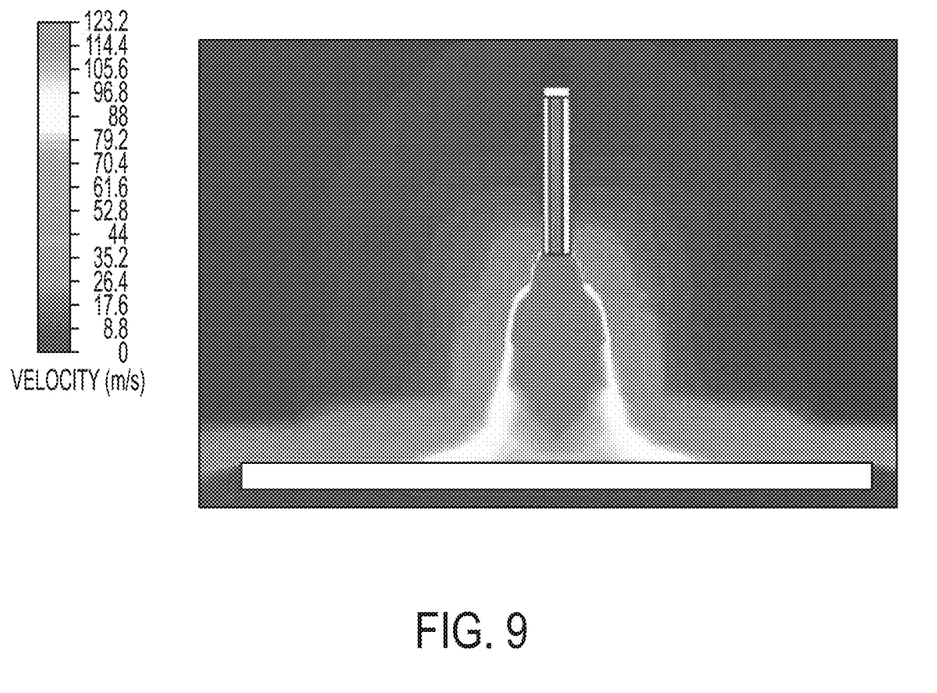
FIG. 9 shows impingement flow to wall jet velocity demonstrating the system's ability to remove particles by all three modes, as seen in Table 3.

The system of the present disclosure leverages both well-known approaches to removing particles from a surface at a distance and a DCE based on the CDC sampling technology. CDC far exceeds any single commercial adsorbent in both breadth of analyte retention and adsorption kinetics for chemical vapors. This allows broad spectrum threat sampling at the large flow rates required for this effort. In some cases, the CDC is fabricated as a thin layer on top of silicon carbide (SiC) foam, thus producing a system with an integral, low-power heating element that provides efficient heat transfer to the analytes for desorption. Therefore, even very large molecular weight analytes can be desorbed. For example, triethyl phosphate (182 g/mol) has been detected at levels below 75 ppt. The prescribed detection limit of 4-50 ng of material correlates well to our previously demonstrated air sampling concentration range. A summary of the system goals and support to meet or exceed them is shown in Table 1. Certain embodiments of the system can transfer liquid and powdered samples to both IMS and quadrupole MS using our integrated collection and desorption technique (See, for example, FIG. 9). In some cases, analyte desorption from the DCE occurs in 30-60 s, and the DCE is conditioned in 30 s, which is well below a 2 minute clear down time requirement.

TABLE 1

| Metric | FIG. of Merit | Technology and Supporting Info |
|---|---|---|
| Non-contact sampling | >2" | Air jet/suction head design utilizing 30-60 CFM suction flow coupled with 20-30 psi disturbance jet for X second(s) duration to create particle lift. |
| Broad threat type | 20 Compounds | High temperature particle vaporization. Directly demonstrated with an organic and inorganic compound(s) (FIG. 8A and FIG. 8B and Table 2). |

TABLE 1-continued

| Metric | FIG. of Merit | Technology and Supporting Info |
|---|---|---|
| Surface types | Nomex, ABS plastic, vinyl, Teflon, packaging tape, cardboard, polyester, cotton, metal, plastic zipper | Initially demonstrated over hard (ABS/corian/Teflon and cloth (polyester/cotton) surfaces with no standoff using 2.8 CFM suction flow. |
| Size of sampled objects | 450 cm$^2$, 1.3 m$^2$, 8 m$^2$ | Due to speed of collection gases (FIG. 10), sample time is limited by operator movement. |
| Sampling efficiency | Deliver >50% | Historical vapor collection data with CDC. |
| Sampling time | <5 seconds | Flow analysis both modeling and experimental. |
| Substrate compatibility | Non-destructive | Air jet/suction head design. Initially demonstrated with no standoff as show in FIG. 9. |
| Clear down time | <2 min. | Collection foams clean automatically during the analysis process. |
| Reliability | ETD requirements | Service and MTBF. |

One of the key challenges in determining the efficiency of a sampling device is generating and characterizing the samples to be analyzed in a repeatable and reliable fashion. Many methods exist for generating reliable and well characterized vapor streams, but very few methods exist for producing and moreover characterizing trace samples of particulate materials. To this end, the use of a fluorescent tagging material was used as a rapid in-house sample characterization tool, which was calibrated through the use of an extremely sensitive ion beam method, nuclear reaction analysis (NRA). NRA uses a high energy proton beam to produce a nuclear reaction with certain nuclei (elements) giving off a characteristic gamma ray. The technique is extremely sensitive providing detection limits in the $10^{13}$-$10^{14}$ atoms per cm$^2$. An ideal choice for this was $^{19}$F, which has 100% isotopic abundance and is present in several common laser dyes like Coumarin 153.

Figure 7:
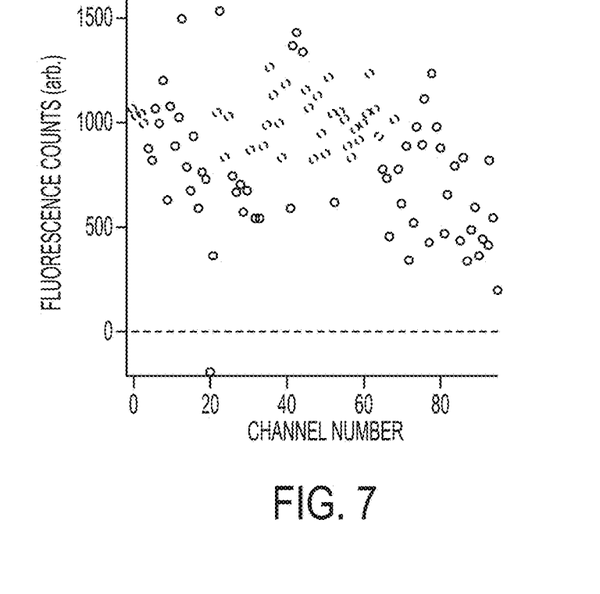
FIG. 7 shows a graph with a background subtracted fluorescence signature from a test sample estimated to be in the ng/cm² range demonstrating the ability to measure the sample concentrations optically.

Particulate samples were prepared using Syloid™ 244 (Syloid), which is a high surface area, fumed silica material with a size distribution ranging from submicron to 20 μm in diameter (7 μm mean diameter), as the carrier material for both the fluorescent tag and the target material. The taggant and target materials are dissolved in solution where concentrations are easily controlled, and then Syloid is added and the solution is allowed to evaporate, resulting in Syloid particles of known size coated in a known quantity of taggant and target. Samples for analysis consist of a known amount of fluorescent tag-loaded Syloid mixed into a known amount of target-loaded material and bare Syloid which behaves simply as a dilution medium. The fluorescence of the sample is measured by a fluorescent plate reader. To test this method, a sample containing 50 ng of target material along with fluorescent taggant was prepared and deposited on a 96 well plate. The estimated active material concentration is in the nanogram per cm$^2$ range. The background subtracted fluorescence is shown in FIG. 7.

The same samples were then collected on double sided tape and sent for NRA analysis to give a real areal density of the fluorescent tag. By knowing the ratio of the fluorescently labeled Syloid to the target-labeled Syloid, the amount of target compound per unit area for very small concentrations was calculated. By correlating NRA-determined concentration to fluorescence, a calibrated method of determining concentration from fluorescence measurements alone is possible. As alternatives to the NRA analysis, particle counting under a microscope as well as solvent extraction and GC/MS analysis are also possible.

Two different methods for producing low concentration samples reliably and reproducibly were tested. The first method utilizes a small air dispersal system in a chamber to aerosolize the particulate material with a shutter to adjust sample exposure time. The second method was an electrospray deposition method which utilizes a stabilized suspension of particles in a liquid which is then sprayed onto a charged surface.

Aerosol deposition is a simple, effective way to produce homogeneous and repeatable samples. A known amount of powder sample is dispersed in a chamber and allowed to settle for a pre-determined amount of time. Since samples contain a range of particle sizes, the particle size and amount of material deposited was controlled via a shutter mechanism. The settling time varied depending on the size of the particles being aerosolized. To control the size of the particles deposited, the shutter's open time was adjusted relative to the release. The amounts of material and the size distribution deposited were determined by the amount of time the sample was open to the chamber for exposure. Simple automation and fixturing rendered this method extremely effective for producing reliable samples in relevant concentrations.

Electrohydrodynamic spraying (electrospray) was an alternative technique to produce samples of known, small concentrations. Electrospray employs a strong electric field to atomize liquids. In its simplest form, electrospray involves applying a voltage from the needle of a syringe to a conductive substrate. Even in this form there are numerous parameters such as flow rate, capillary diameter, solution dielectric constant, and voltage, which can be tuned for use in a wide range of applications. Further adaptability has come from recent advances with incorporating electrospray into printing systems to provide more control, simpler automation, and directed deposition. This versatility makes electrospray ideal for the deposition of very small amounts of a wide variety of samples. By creating very dilute suspensions and spraying for short periods of time, nanograms of material can be deposited. In one example, 10 μm tin particles were deposited which were suspended in a mixture of water and 1-butanol with DARVAN-821A as a stabilizing agent at 0.5 mg/ml. The Syloid materials from which our samples were derived may be stabilized by functionalization with different organosilane ligands.

Figure 8A:
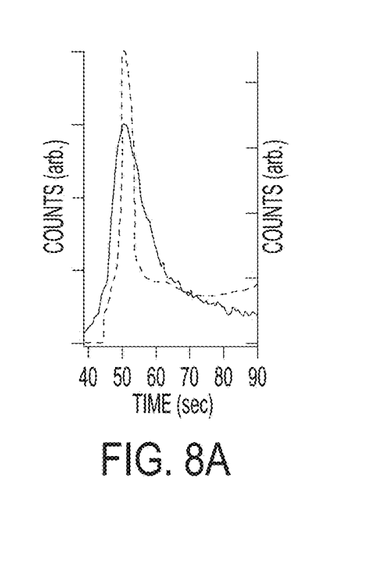
FIG. 8A shows Quadrupole Mass Spectrometer (MS) ammonium nitrate response from liquid (red) and powder (black).
Figure 8B:
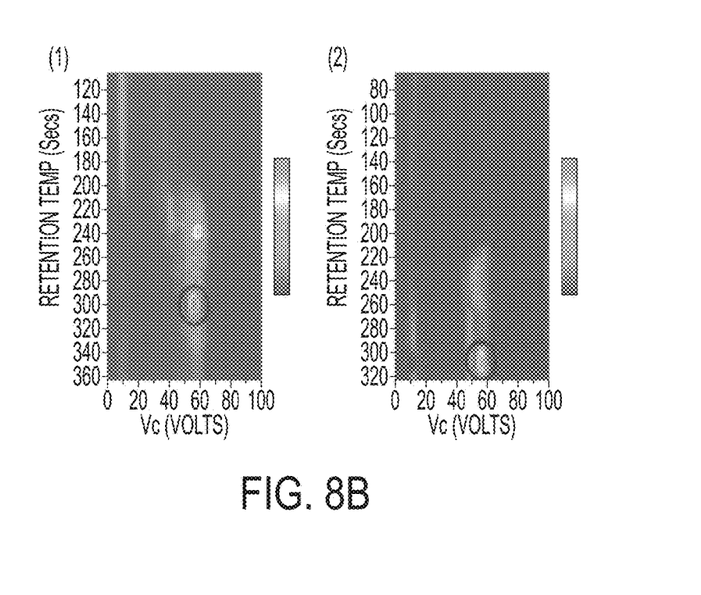
FIG. 8B shows a dinitrotoluene (DNT) signal from an ion mobility spectrophotometer (IMS) instrument for a liquid (1) and a solid (2) sample.

Three fundamental processes are involved in the PS and HVMS systems: extraction of chemicals from surfaces, collection in the DCE, and delivery to the analytical instrument. To characterize the total system performance, detector response was characterized. Instrument response curves were generated for the listed test compounds (Table 2) by introducing liquid samples to the SiC foam. To characterize the transfer efficiency of the particles to the detector, sample was applied directly to the particle collection foams via the sample preparation method of choice. The sample was then desorbed into the instrument and the response measured, providing a transfer efficiency for that analyte and that step in the process. FIG. 8A and FIG. 8B demonstrates the ability to deposit liquid and solid samples onto the foam substrates to characterize the transfer efficiency for both quadrupole MS and IMS. FIG. 8A shows the instrument response to 5 μg of ammonium nitrate in liquid form (taller peak) and 30 μg adsorbed on Syloid. The data was collected on larger quantities of material due to the instrument's detection limit near 500 ng; these amounts are not indicative of an ultimate limit of detection for the system. FIG. 8B shows the IMS instrument response to 5 μg of DNT in liquid (1) and 30 μg adsorbed on Syloid (2). The peaks for the DNT are circled. These data demonstrate the viability of delivering solid samples to both analysis systems. Some of the other relevant compounds successfully detected to date are summarized in Table 2.

TABLE 2

Some of the analytes tested to date. A check indicates successful detection. No chemicals were attempted but not detected.

| Chemical Class | Analyte | IMS Particle | IMS Vapor | Quad MS Particle | Quad MS Vapor |
|---|---|---|---|---|---|
| Nitro aromatic | dinitrotoluene | ✓ | ✓ | ✓ | ✓ |
| Inorganic salt | ammonium nitrate | — | — | ✓ | — |
| Plastic explosive | dimethyldinitrobutane | — | — | ✓ | — |
| Peroxides | ditertbutyl-peroxide | ✓ | ✓ | ✓ | ✓ |
| Homemade | acetone | ✓ | ✓ | ✓ | ✓ |
| ANFO | diesel | — | — | ✓ | ✓ |

Optimization of transfer efficiency depends heavily on the instrument chosen. Known important parameters include desorption temperature, desorption time, carrier gas flow and carrier gas composition (i.e. air, helium, carbon dioxide etc.). In the case of vacuum desorption into a mass spectrometer, the interface and conductance paths are important. The instrument interfaces for the PS and HVMS are very similar and as such the transfer optimization commute between both the PS and HVMS. Once the transfer efficiency and instrument response have been characterized, the instruments are used to measure the collection efficiency of the materials off the various surfaces. Surfaces attempted to date include plastics, cotton, and cotton blend fabrics, and a plastic zipper (See, for example, FIG. 8A). It should be noted that these items were not sampled at a standoff and the amounts of analyte were not characterized.

The collection efficiency of the foam materials with respect to vapors has been shown to be outstanding when testing against chemical warfare agents and simulants. Collection of particulates has been demonstrated but not yet quantified. To check for breakthrough of the particles, a filter membrane was placed behind the foam element during collections and then the filter membrane was analyzed using fluorescence measurements in a similar fashion to the way the samples were characterized.

The key parameters dealing with surface extraction are determining the amount of suction and agitation flow required to efficiently extract the particulate materials from a surface. Initial designs were guided by flow dynamics calculations. The components were created in silico and optimized using computational flow dynamics (CFD) calculations to provide the maximum lifting force at the 2 inch stand-off required. A force analysis showed that there are three modes by which a particle can be moved from a surface: direct lift, sliding, and rolling.

Table 3 shows three different models that calculate the air velocity required for these three modes, considering such factors as the lift force, gravitational force, adhesion force, and drag force. Some baseline nozzle parameters are shown in Table 4. Initial calculations show that an air impingement velocity of 77 m/s (the approximate air speed of a medium grade leaf blower) was needed. A concept nozzle and puffing unit provided choked flow with a supply pressure of 20 PSI and a ⅛" diameter nozzle producing an exit velocity of 340 m/s (sonic). At 2" stand-off, the resulting velocity is about ½ nozzle exit velocity or 170 m/s. CFD analysis showed the required exit flow achieved the radial wall jet velocity in the tables below. In order to produce a radial wall jet velocity of 77 m/s (about at the transition of yellow to green in FIG. 9), the impingement exit velocity would need to be about 123 m/s. This velocity satisfies all modes of release and can be generated by the system of the present disclosure.

TABLE 3

Calculated air velocities for different modes of particle removal.

| Detachment | SS70 | GL72 | GL32 |
|---|---|---|---|
| Direct Lift Off | 58 m/s | 77 m/s | 133 m/s |
| Sliding | 41 m/s | 58 m/s | 94 m/s |
| Rolling | 3 m/s | 7 m/s | 14 m/s |

TABLE 4

Initial estimated nozzle parameters.

| Parameter | PS | HVMS |
|---|---|---|
| Surface Velocity | 170 m/s | 170 m/s |
| Suction Flow | 30 CFM | 130 CFM |
| Nozzle air volume | 90% Vacuum flow | 90% Vacuum flow |
| Impingement | Sonic | Sonic |
| Orifice Diameter | 0.125" | 0.125" |
| Supply Pressure | 20 psi | 20 psi |
| Area sampled | 450 cm2 | 0.82, 1.3, and 8 m$^2$ |

CFD tells us how a lifted particle then might interact with the suction flow field. The PS and HVMS nozzle design (See, for example, FIG. 10) and flow parameters are within historical norms in comparison to aerodynamic sampling over a short stand-off distance. At its exit (marked A), the flow rate of the jet can be calculated, and at 30 psi the flow at the nozzle exit is sonic, creating a turbulent jet with a round cross section spreading at a 12-degree half-angle as shown in the sketch, due to entrainment of surrounding air. The wall jet is also turbulent and grows with distance y from the impingement point B due to entrainment. Once this occurs over the distance from points B to C, the entire chore of the suction generated by the sampler is to cause the radial wall jet to separate from the surface at C and thus be carried into the sampler inlet D, along with particles removed from the surface.

Figure 10:
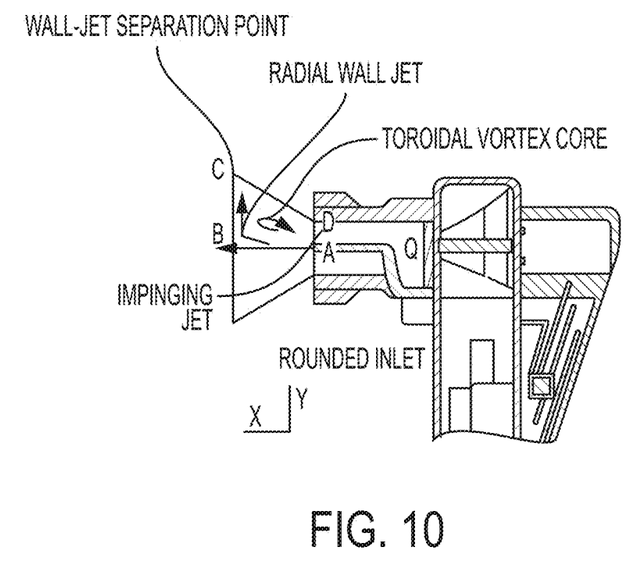
FIG. 10 shows a perspective view of one embodiment of a nozzle design.

Along with air impingement, infrared flash excitation is incorporated into the nozzle design. The IR flash enhances vapor emission from surface solids, allowing trace vapors of low volatile compounds to be captured by the extreme sensitivity of CDC.

Figure 11A:
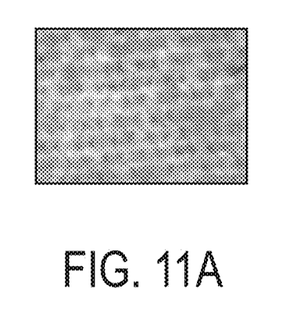
FIG. 11A shows a fabric sample before and FIG. 11B shows a fabric sample after sampling; no visible damage.
Figure 11B:
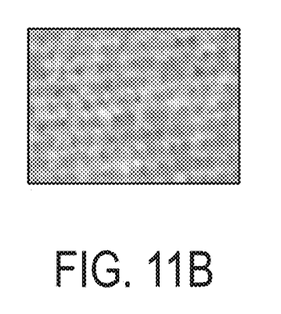

During testing, samples were examined via microscopy to ensure no damage was occurring during sampling. FIG. 11A shows a fabric sample before and FIG. 11B shows the fabric sample after sample collection. No damage is evident after vacuuming the particulates from the fabric.

While the present invention has been described in connection with the preferred embodiments of the various figures, it is to be understood that other similar embodiments may be used or modifications or additions may be made to the described embodiment for performing the same function of the present invention without deviating therefrom. Therefore, the present invention should not be limited to any single embodiment, but rather construed in breadth and scope in accordance with the recitation of the appended claims.

What is claimed is:

1. A method for detection and identification of one or more chemicals comprising the steps of:
providing a carbide-derived carbon dual preconcentrator, wherein the dual preconcentrator comprises one or more substrates, one of the substrates comprising silicon carbide and a carbide derived carbon skin on a surface of the silicon carbide substrate, the dual preconcentrator comprising a base configured to support a first insert and a second insert, the base further comprising electrical contacts for use in applying an electrical current to the inserts;
the dual preconcentrator configured for
collecting a sample of the one or more chemicals, wherein the sample is in a gaseous, liquid, particulate, or aerosol phase;
desorbing the one or more chemicals from the carbide derived carbon skin on the surface of the substrate when resistively heated via the electrical contacts;
processing said sample of the one or more chemicals; and
introducing said processed one or more chemicals into a chemical analysis instrument for detection and identification of the one or more chemicals.

2. The method of claim 1, wherein the substrate is a solid, a fiber, a powder, open cell foam, or a mesh.

3. The method of claim 1, wherein both particulate and vapor samples are collected and analyzed simultaneously via the first and second inserts.

4. The method of claim 2, wherein the substrate is patterned.

5. A system for use in detecting a chemical comprising
a power source;
an inlet and an outlet;
one or more proximity sensors configured to detect a proper testing distance;
a motor control system for controlling an impeller attached to a motor;
a dual preconcentrator element, wherein the dual preconcentrating element comprises a base configured to support a first insert and a second insert, the base further comprising electrical contacts for use in applying an electrical current to the inserts, one of the inserts comprising a carbide-derived carbon skin on a silicon carbide substrate that when resistively heated via the electrical contacts desorbs previously adsorbed one or more chemicals,
wherein the one or more chemicals are in a gaseous, liquid, particulate, or aerosol phase;
an IR flash ring; and
an air puffing unit.

6. The system of claim 5, further comprising a rapid first alarm (RFA) detector.

7. The system of claim 5, further comprising a docking station.

8. The method of claim 5, wherein the substrate comprises a foam, a solid, a fiber, a powder, or a mesh.

* * * * *